US012808879B2

(12) United States Patent
E et al.

(10) Patent No.: US 12,808,879 B2
(45) Date of Patent: Nov. 24, 2026

(54) METHODS FOR CHARACTERIZING HOST-CELL PROTEINS

(71) Applicant: Regeneron Pharmaceuticals, Inc., Tarrytown, NY (US)

(72) Inventors: Sook Yen E, Croton-on-Hudson, NY (US); Yunli Hu, Tarrytown, NY (US); Rosalynn Molden, Shoreline, WA (US); Haibo Qiu, Millwood, NY (US); Ning Li, New Canaan, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 602 days.

(21) Appl. No.: 18/208,394

(22) Filed: Jun. 12, 2023

(65) Prior Publication Data

US 2023/0408527 A1 Dec. 21, 2023

Related U.S. Application Data

(60) Provisional application No. 63/353,401, filed on Jun. 17, 2022.

(51) Int. Cl.
*G01N 33/68* (2006.01)
*G01N 30/72* (2006.01)

(52) U.S. Cl.
CPC ..... *G01N 33/6848* (2013.01); *G01N 30/7233* (2013.01); *G01N 33/6845* (2013.01); *G01N 2560/00* (2013.01)

(58) Field of Classification Search
CPC ........... G01N 33/6848; G01N 30/7233; G01N 33/6845; G01N 2560/00; G01N 2333/918; G01N 33/6842
See application file for complete search history.

(56) References Cited

U.S. PATENT DOCUMENTS

2021/0008199 A1* 1/2021 Zhang ............ C12Y 301/01053
2021/0109107 A1* 4/2021 Zheng .................... G01N 33/94
2021/0268073 A1 9/2021 Xiao et al.

FOREIGN PATENT DOCUMENTS

WO WO 2021/076735 A1 4/2021

OTHER PUBLICATIONS

Huang et al. A novel sample preparation for shotgun proteomics characterization of HCPs in antibodies. Anal. Chem. 2017;89:5436-5444.*

Ma et al. Sensitive, rapid, robust, and reproducible workflow for host cell protein profiling in biopharmaceutical process development. J. Proteome Res. 2020;19:3396-3404.*

Li Xuanwen et al: "Profiling Active Enzymes for Polysorbate Degradation in Biotherapeutics by Activity-Based Protein Profiling", Analytical Chemistry, May 25, 2021 (May 25, 2021), pp. 1-9, XP055809534, US, ISSN: 003-2700, DOI: 10.1021/acs.analchem.1c00042, Retrieved from the Internet: URL:https://pubs.acs.org/doi/pdf/10.1021/acs.analchem.1c00042>, p. 1-5; figure 2.

Chen Yunqiu et al: "A Highly Sensitive LC-MS/MS Method for Targeted Quantitation of Lipase Host Cell Proteins in Biotherapeutics", Journal of Pharmaceutical Sciences, vol. 110, No. 12, Aug. 28, 2021 (Aug. 28, 2021), pp. 3811-3818.

Reid O'Brien Johnson et al: "Combination of FAIMS, Protein A Depletion, and Native Digest Conditions Enables Deep Proteomic Profiling of Host Cell Proteins in Monoclonal Antibodies", Analytical Chemistry, vol. 92, No. 15, Jul. 6, 2020 (Jul. 6, 2020), pp. 10478-10484, XP055767405, US, ISSN: 0003-2700, DOI: 10.1021/acs.analchem.0c01175 PG10478-10482; figure 1.

Thermofischer Scientific: "The Switch Is on: from triple quadrupoles and Q-TOF to Orbitrap High Resolution Mass Spectrometry," Dec. 31, 2017 (Dec. 31, 2017), pp. 1-5.

E Sook Yen et al: "Identification and Quantification of a Problematic Host Cell Protein to Support Therapeutic Protein Development", Journal of Pharmaceutical Sciences, vol. 112, No. 3, Oct. 9, 2022 (Oct. 9, 2022), pp. 673-679.

International Search Report Application No. PCT/2023/025022, Filing Date Jun. 12, 2023, Date of mailing Sep. 18, 2023.

* cited by examiner

*Primary Examiner* — Lynn Y Fan
(74) *Attorney, Agent, or Firm* — Schwabe, Williamson & Wyatt PC; Angela Guo

(57) ABSTRACT

A practical and effective method for low abundance host cell protein (HCP) identification and quantification, which facilitates the downstream purification process in eliminating potentially problematic HCPs. In particular, the method comprises performing a native digestion followed by characterization using Multiple Reaction Monitoring approach.

20 Claims, 10 Drawing Sheets

| Protein Name | Accession# | mAb1 | | mAb2 | | mAb3 | |
|---|---|---|---|---|---|---|---|
| | | Process 1 | Process 2 | Process 1 | Process 2 | Process 1 | Process 2 |
| Peroxiredoxin-1 | Q9JKY1 | 63.7 | 96.6 | 0.1 | 0.3 | 0.4 | 2.2 |
| Liver carboxylesterase 1-like protein (CES-1L)* | A0A061IFE2 | 42.5 | 10.2 | 0.0 | 0.0 | 0.0 | 0.0 |
| Metalloproteinase inhibitor 1 (TIMP1) | G3IBH0 | 20.7 | 23.1 | 4.7 | 2.5 | 2.8 | 5.6 |
| U4/U6 small nuclear ribonucleoprotein Prp4 | G3HI03 | 17.2 | 23.3 | 0.0 | 0.0 | 0.1 | 0.0 |
| Putative phospholipase B-like 2 (PLBD2) | G3I6T1 | 10.3 | 18.6 | 0.3 | 0.0 | 0.0 | 0.0 |
| Glutathione S-transferase Mu 6 | G3IKC3[2] | 7.3 | 11.5 | 6.3 | 3.9 | 8.4 | 9.5 |
| C-C motif chemokine | G3GTT2 | 7.1 | 5.9 | 7.7 | 5.6 | 3.9 | 3.4 |
| Peptidyl-prolyl cis-trans isomerase | G3H533 | 6.2 | 3.2 | 5.3 | 2.9 | 2.9 | 1.8 |
| Insulin-like growth factor-binding protein 4 | G3I5N6 | 4.1 | 5.8 | 3.5 | 4.1 | 4.4 | 4.1 |
| Putative hydrolase RBBP9 | G3GVW2 | 3.5 | 7.5 | 0.0 | 0.0 | 0.0 | 0.0 |
| Complement C1r-A subcomponent | G3GUR1 | 3.4 | 10.4 | 2.8 | 1.8 | 2.7 | 2.8 |
| Glutathione S-transferase P | G3I3Y6 | 2.5 | 4.5 | 0.3 | 0.1 | 0.2 | 0.3 |
| Protein S100 | G3HUU6 | 2.3 | 6.4 | 6.9 | 4.4 | 8.0 | 6.6 |
| Beta-2-microglobulin | Q9WV24 | 2.3 | 5.2 | 1.4 | 1.6 | 1.5 | 2.4 |
| Aimnoacylase-1A | G3H892 | 2.2 | 2.3 | 0.0 | 0.0 | 0.0 | 0.0 |
| Protein-glutamine gamma-glutamyltransferase 2 | G3GXZ0 | 2.1 | 2.7 | 0.4 | 0.2 | 0.2 | 0.3 |
| Annexin | G3IG05 | 1.5 | 1.5 | 1.9 | 1.2 | 2.5 | 1.5 |

Low High

FIG. 2

| Protein Name | Accession# | mAb1 | | mAb2 | | mAb3 | |
|---|---|---|---|---|---|---|---|
| | | Process 1 | Process 2 | Process 1 | Process 2 | Process 1 | Process 2 |
| G-protein coupled receptor 56 | G3I3K5 | 1.4 | 1.6 | 1.1 | 0.7 | 0.9 | 1.2 |
| Cathepsin D | G3I4W7 | 1.3 | 2.4 | 0.0 | 0.0 | 0.0 | 0.0 |
| Serine protease HTRA1 | G3IBF4 | 1.3 | 3.4 | 0.1 | 0.0 | 0.2 | 0.0 |
| Inter-alpha-trypsin inhibitor heavy chain H5 | G3GR64 | 1.2 | 2.2 | 2.9 | 1.9 | 1.5 | 2.3 |
| 78 kDa glucose-regulated protein | G3I8R9 | 1.0 | 1.2 | 0.5 | 0.7 | 0.3 | 0.2 |
| Fructose-bisphosphate aldolase | G3I3X4 | 1.0 | 1.2 | 0.7 | 0.7 | 0.7 | 1.0 |

Low High

FIG. 2
CONTINUED

METHODS FOR CHARACTERIZING HOST-CELL PROTEINS

CROSS-REFERENCE TO RELATED APPLICATIONS

This application claims the benefit of U.S. Provisional Patent Application No. 63/353,401, filed Jun. 17, 2022, which is incorporated by reference herein in its entirety.

FIELD

The present invention generally pertains to characterizing host-cell proteins.

BACKGROUND

Protein-based biopharmaceutical products have emerged as important drugs for the treatment of cancer, autoimmune disease, infection and cardiometabolic disorders, and they represent one of the fastest growing product segments of the pharmaceutical industry. Bringing a protein-based biotherapeutic to the clinic can be a multiyear undertaking requiring coordinated efforts throughout various research and development disciplines, including discovery, process and formulation development, analytical characterization, and pre-clinical toxicology and pharmacology. Protein-based biopharmaceutical products must meet very high standards of purity. Thus, it can be important to monitor any impurities in such biopharmaceutical products at different stages of drug development, production, storage and handling.

For example, host cell proteins (HCPs) can be present in protein-based biopharmaceuticals which are developed using cell-based systems. The presence of HCPs in drug products needs to be monitored and can be unacceptable above a certain amount. Analytical methods for assays for characterization of HCPs should display sufficient accuracy and resolution. Direct analysis can require isolation of the product in a sufficiently large amount for the assay, which is undesirable and has only been possible in selected cases. Hence, it is a challenging task to determine the workflow and analytical tests to characterize HCPs in a sample matrix when mixed with overwhelmingly high concentration of an active drug. From the foregoing it will be appreciated that a need exists for improved methods for characterizing and monitoring HCPs at various stages of a biopharmaceutical process.

SUMMARY

A key criterion in developing biopharmaceutical products can be to monitor impurities in the product. When such impurities do occur, their characterization constitutes an important step in the bioprocess.

Exemplary embodiments disclosed herein satisfy the aforementioned demands by providing methods for characterizing host-cell protein(s).

In one exemplary embodiment, the present invention discloses a method for identifying and quantifying at least one host-cell protein in a sample matrix including a protein of interest, comprising adding a digestion agent under native conditions to obtain a native digested sample; and analyzing the native digested sample using a triple quadrupole mass spectrometer to identify a peptide specific to said at least one host-cell protein, wherein said triple quadrupole mass spectrometer is run to obtain multiple reaction monitoring for at least one precursor-product ion for said peptide.

In one aspect, the digestion agent is trypsin. In another aspect, the digestion agent can be one or more of trypsin, endoproteinase Arg-C, endoproteinase Asp-N, endoproteinase Glu-C, outer membrane protease T (OmpT), immunoglobulin-degrading enzyme of Streptococcus pyogenes (IdeS), chymotrypsin, pepsin, thermolysin, papain, pronase, and protease from *Aspergillus saitoi*. Such a digestion agent is able to perform native digestion of the sample.

In one aspect, the digestion agent is about 0.4 μg of trypsin. In another aspect, the digestion agent is about 0.01 μg to about 0.1 μg of trypsin.

In one aspect, native conditions include using the digestion agent such that the protein of interest is digested less than said host cell protein.

In one aspect, the triple quadrupole mass spectrometer is coupled to liquid chromatography. The liquid chromatography can be a rapid resolution liquid chromatography (RRLC), ultra-performance liquid chromatography (UPLC), ultra-fast liquid chromatography (UFLC) and nano liquid chromatography (nLC).

In one aspect, the mass spectrometer is run in a positive mode.

In one aspect, the method also comprises performing enrichment of the at least one host cell protein or depletion of the protein of interest. The enrichment can be performed using protein A depletion of the protein of interest or using a molecular weight cut-off.

In one aspect, the lower limit of quantification of the method is less than about 1 ppm. In another aspect, the lower limit of quantification of the method is less than about 0.05 ppm.

In one exemplary embodiment, the present invention discloses a method for identifying at least one host-cell protein in a sample matrix including a protein of interest, comprising adding a digestion agent under native conditions to obtain a native digested sample; analyzing the native digested sample using a triple quadrupole mass spectrometer to identify a peptide specific to said at least one host-cell protein, wherein said triple quadrupole mass spectrometer is run to obtain multiple reaction monitoring for at least one precursor-product ion for said peptide; and quantifying an amount of said at least one host-cell protein by quantifying an amount of said peptide by utilizing an isotopically-enriched peptide having the same amino acid sequence as that of said peptide to calibrate the quantitation of said peptide, and utilizing a standard comprising a known concentration of peptide to calibrate the quantitation of said peptide.

In one aspect, the digestion agent is trypsin. In another aspect, the digestion agent can be one or more of trypsin, endoproteinase Arg-C, endoproteinase Asp-N, endoproteinase Glu-C, outer membrane protease T (OmpT), immunoglobulin-degrading enzyme of Streptococcus pyogenes (IdeS), chymotrypsin, pepsin, thermolysin, papain, pronase, and protease from *Aspergillus saitoi*. Such a digestion agent is able to perform native digestion of the sample.

In one aspect, the digestion agent used is about 0.4 μg of trypsin. In another aspect, the digestion agent used is about 0.01 μg to about 0.1 μg of trypsin In one aspect, the native conditions include using the digestion agent such that the protein of interest is digested less than the host cell protein.

In one aspect, the triple quadrupole mass spectrometer is coupled to liquid chromatography. The liquid chromatography can be a rapid resolution liquid chromatography (RRLC), ultra-performance liquid chromatography (UPLC), ultra-fast liquid chromatography (UFLC) and nano liquid chromatography (nLC).

In one aspect, the mass spectrometer is run in a positive mode.

In one aspect, the method also comprises performing enrichment of the at least one host cell protein or depletion of the protein of interest. The enrichment can be performed using protein A depletion of the protein of interest or using a molecular weight cut-off.

In one aspect, the lower limit of quantification of the method is less than about 1 ppm. In another aspect, the lower limit of quantification of the method is less than about 0.05 ppm.

These, and other, aspects of the invention will be better appreciated and understood when considered in conjunction with the following description and the accompanying drawings. The following description, while indicating various embodiments and numerous specific details thereof, is given by way of illustration and not of limitation. Many substitutions, modifications, additions, or rearrangements may be made within the scope of the invention.

BRIEF DESCRIPTION OF THE DRAWINGS

FIG. 2 shows a table of HCPs identified in mAb1, mAb2 and mAb3 process 1 and process 2 by native digestion (abundance in ppm), wherein the * indicates selected peptides shared by multiple liver carboxylesterase isoforms and the heatmap is colored by HCP abundance, ranging from lowest value (green) to highest value (red).

DETAILED DESCRIPTION

Figure 1:
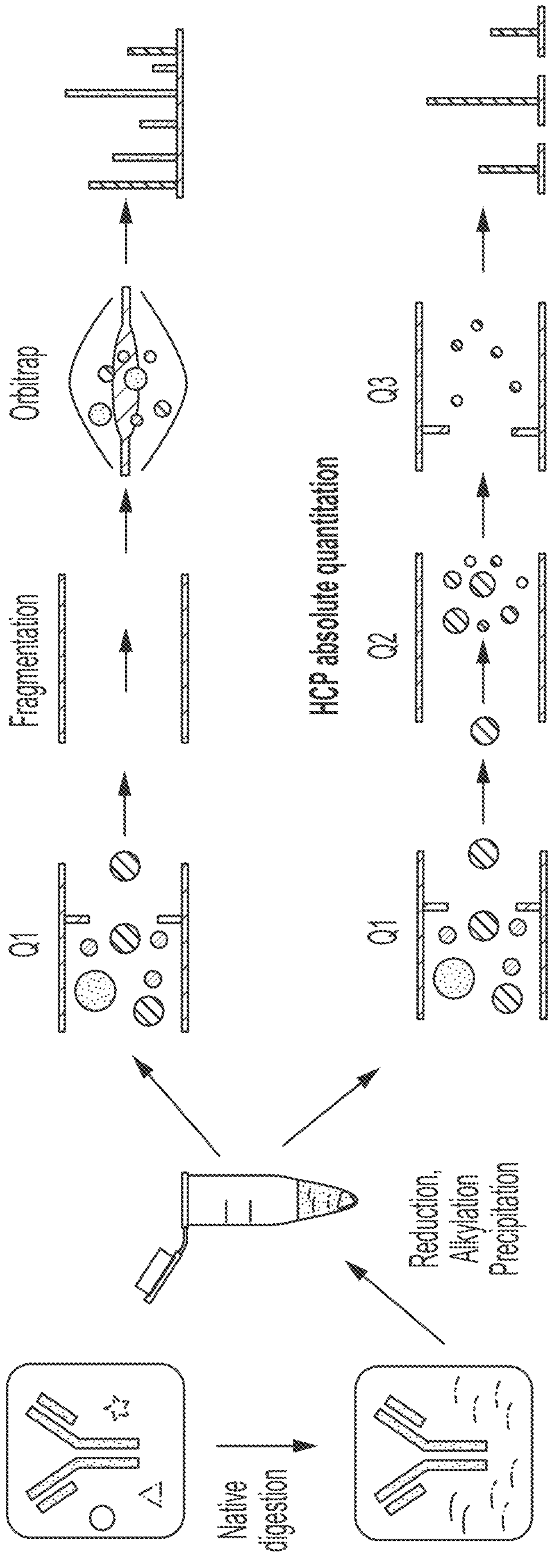
FIG. 1 shows a schematic of HCP profiling and quantification workflow according to an exemplary embodiment.

Host cell proteins (HCPs) are process-related impurities introduced during therapeutic protein production. Recent studies have shown that trace level HCPs may degrade therapeutic products or excipients, induce adverse events in patients and affect the product quality and shelf life. For example, protease such as Cathepsin D has been reported to degrade mAbs and causes fragmentation in drug product (Bee et al., Trace levels of the CHO host cell protease cathepsin D caused particle formation in a monoclonal antibody product, biotechnology Progress 31(5) (2015); Robert et al., Degradation of an Fc-fusion recombinant protein by host cell proteases: identification of a CHO Cathepsin D protease, Biotechnology Bioengineering 104 (6) (2009)). Hexosaminidase B has been shown to cleave GlcNAc of glycan and change the glycan profile of therapeutic proteins (Li et al., Identification and characterization of a residual host cellprotein hexosaminidase B associated with N-glycandegradation during the stability study of a therapeutic recombinant monoclonal antibody product, Biotechnology and Bioengineering 37 (2020)). Lipases or esterases represent another group of high-risk HCPs that may cleave the ester bond of polysorbate (PS), which is an excipient commonly used to formulate therapeutic proteins. The ester bond of PS can be hydrolyzed by lipases due to the structural similarity to triglycerides, which results in releasing of free fatty acids (FFA). The accumulation of FFA may induce the formation of particles and hence reduce the shelf life of a therapeutical product.

To support process development and mitigate risks, effective methods with high sensitivity and fast turnaround time are required to identify and quantify these problematic HCPs. The LC-MS/MS-based proteomics method has evolved as an important tool to identify the HCPs and provide guidance to the downstream purification process. To overcome the limitation of the dynamic range of the mass spectrometry, sample preparation methods that reduce the high abundance drug substance (DS) or enrich low abundance HCPs have been implemented in the HCP workflow. These methods include native digestion (Huang et al., A Novel Sample Preparation for Shotgun Proteomics Characterization of HCPs in Antibodies, Analytical Chemistry 89(10) (2017); Yang et al., Versatile LC—MS-Based Workflow with Robust 0.1 ppm Sensitivity for Identifying Residual HCPs in Biotherapeutic Products, Analytical Chemistry 94 (2022)), ProteoMiner (Chen & Li, Improved host cell protein analysis in monoclonal antibody products through ProteoMiner, Analytical Biochemistry 610 (2020)), Protein A depletion (Thompson et al., Improved detection of host cell proteins (HCPs) in a mammalian cell-derived antibody drug using liquid chromatography/mass spectrometry in conjunction with an HCP-enrichment strategy, Rapid communications in mass spectrometry 28(8) (2014); Johnson et al., Combination of FAIMS, Protein A Depletion, and Native Digest Conditions Enables Deep Proteomic Profiling of Host Cell Proteins in Monoclonal Antibodies, Analytical Chemistry 92(15) (2020); Madsen et al., Toward the complete characterization of host cell, proteins in biotherapeutics via affinity depletions, LC-MS/MS, and multivariate analysis, mAbs 7(6) (2015)), and molecular weight cutoff (Chen et al., Improved Host Cell Protein Analysis in Monoclonal Antibody Products through Molecular Weight Cutoff Enrichment, Analytical Chemistry 92(5) (2020)).

In addition, sample fractionation (Wang et al., Enhancing Host-Cell Protein Detection in Protein Therapeutics Using HILIC Enrichment and Proteomic Analysis, Analytical Chemistry 92 (2020); Bomans et al., Identification and Monitoring of Host Cell Proteins by Mass Spectrometry Combined with High Performance Immunochemistry Testing, PLOS ONE 8(11) (2013); Soderquist et al., Development of Advanced Host Cell Protein Enrichment and Detection Strategies to Enable Process Relevant Spike Challenge Studies, American Institute of Chemical Engineers 31(4) (2015)) and longer gradients (Nie et al., Simple and Sensitive Method for Deep Profiling of Host Cell Proteins in Therapeutic Antibodies by Combining Ultra-Low Trypsin Concentration Digestion, Long Chromatographic Gradients, and BoxCar Mass Spectrometry Acquisition, Analytical Chemistry 93 (2021)) or 2D-LC (A 2D LC-MS/MS Strategy for Reliable Detection of 10-ppm Level Residual Host Cell Proteins in Therapeutic Antibodies, Analytical Chemistry 90 (2018); Farrell et al., Quantitative Host Cell Protein Analysis Using Two Dimensional Data Independent LC-$MS^E$, Analytical Chemistry 87 (2015)) have also been applied to reduce the dynamic range and improve the sensitivity. Moreover, different MS acquisition methods, such as BoxCar (Nie et al., supra) and AIMS (Huang et al., Toward unbiased identification and comparative quantification of host cell protein impurities by automated iterative LC-MS/MS (HCP-AIMS) for therapeutic protein development, Journal of Pharmaceutical and Biomedical Analysis 200 (2021)), have been implemented as novel workflows for HCP analysis and improve the HCP identification.

Recently, activity-based protein profiling (ABPP) methods have been developed to enrich HCPs with lipase activity (Li et al., Profiling Active Enzymes for Polysorbate Degradation in Biotherapeutics by Activity-Based Protein Profiling, Analytical Chemistry 93 (2021); Zhang, Rapid Polysorbate 80 Degradation by et al., Liver Carboxylesterase in a Monoclonal Antibody Formulated Drug Substance at Early Stage Development, Journal of Pharmaceutical Sciences 109(11) (2020)). These approaches allow the detection of low abundance lipases and provide insights into enzymatic activity. This strategy has been successfully utilized to identify high-risk HCPs that impact PS degradation, such as liver carboxylesterase (CES), Sialic acid acetylesterase (SIAE), Lysophospholipase 2 (LPLA2), Lipoprotein lipase (LPL), and Lysosomal acid lipase (LIPA).

Targeted MS quantitation methods, such as parallel reaction monitoring (PRM) and multiple reaction monitoring (MRM), also have been developed to determine the problematic HCP levels and ensure process consistency. LC-MRM-based quantitation methods have been utilized to monitor putative phospholipase B-like 2 (PLBD2), LPLA2, and LPL with a detection limit of 1 ppm (Gao et al., Targeted Host Cell Protein Quantification by LC-MRM Enables Biologics Processing and Product Characterization, Analytical Chemistry 92 (2020)). Chen et al reported a similar MRM method to monitor PLBD2, LPL, and LIPA with sensitivity between 0.8 ppm to 2.2 ppm (Chen et al., A Highly Sensitive LC-MS/MS Method for Targeted Quantitation of Lipase Host Cell Proteins in Biotherapeutics, Pharmaceutical Biotechnology 110 (2021)). The LLOQ of those current MRM absolute quantification methods is still relatively high, considering certain lipases are even active at sub-ppm or ppb levels. Feng et al further implemented native digestion in MRM quantification workflow and improved the sensitivity to 0.1 ppm (Feng et al., Versatile LC-MS-Based Workflow with Robust 0.1 ppm Sensitivity for Identifying Residual HCPs in Biotherapeutic Products, Analytical Chemistry 94 (2022)). Even though the quantification details were not demonstrated, it demonstrated the possibility of enhancing the MRM method sensitivity via HCP enrichment.

These studies may be inadequate to identify and quantify the HCPs at an extremely low level, especially below 1 ppm or even below 0.1 ppm. To effectively identify and quantify low abundance problematic HCPs, the present invention provides a HCP analysis workflow. Highly sensitive and robust HCP profiling was achieved by native digestion-based method, which implements a library generated from upstream pools to facilitate the HCP identification in DS. UPLC-MRM-MS method is utilized to monitor the problematic HCPs to ensure product safety and process consistency. A case study of using this workflow for PS80 degradation root cause investigation and support the process development is presented. A highly sensitive targeted MRM method that incorporates native digestion to deplete antibody protein with a lower limit of quantification (LLOQ) of 0.05 was developed for monitoring the level of a specific problematic HCP, CES, in this study. The workflow successfully enables the identification and quantification of the problematic HCP, which induces the PS80 degradation, and effectively supports the downstream processes. This workflow provides a sensitive and robust analysis strategy, which can be easily adapted to monitor other problematic HCPs and mitigate the risks caused by low-level HCPs.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described. All publications mentioned are hereby incorporated by reference.

The term "a" should be understood to mean "at least one"; and the terms "about" and "approximately" should be understood to permit standard variation as would be understood by those of ordinary skill in the art; and where ranges are provided, endpoints are included.

In some exemplary embodiments, the disclosure provides methods for characterizing a host-cell protein. As used herein, the term "host-cell protein" includes protein derived from the host cell and can be unrelated to the desired protein of interest. Host-cell protein can be a process-related impurity which can be derived from the manufacturing process and can include the three major categories: cell substrate-derived, cell culture-derived and downstream derived. Cell substrate-derived impurities include, but are not limited to, proteins derived from the host organism and nucleic acid (host cell genomic, vector, or total DNA). Cell culture-derived impurities include, but are not limited to, inducers, antibiotics, serum, and other media components. Downstream-derived impurities include, but are not limited to, enzymes, chemical and biochemical processing reagents (e.g., cyanogen bromide, guanidine, oxidizing and reducing agents), inorganic salts (e.g., heavy metals, arsenic, nonmetallic ion), solvents, carriers, ligands (e.g., monoclonal antibodies), and other leachables.

In some exemplary embodiments, the host-cell protein can have a pI in the range of about 4.5 to about 9.0. In one aspect, the pI can be about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the disclosure provides methods for characterizing a host-cell protein in a sample matrix. In one aspect, the sample matrix can be obtained from any step of the bioprocess, such as, culture cell culture fluid (CCF), harvested cell culture fluid (HCCF), process performance qualification (PPQ), any step in the downstream processing, drug substance (DS), or a drug product (DP) comprising the final formulated product. In another aspect, the sample matrix can be selected from any step of the downstream process of clarification, chromatographic purification, viral inactivation, or filtration. In one other aspect, the drug product can be selected from manufactured drug product in the clinic, shipping, storage, or handling.

In some exemplary embodiments, the types of host-cell proteins in the composition can be at least two.

In some exemplary embodiments, the sample matrix can further comprise a protein of interest. As used herein, the term "protein" or "protein of interest" can include any amino acid polymer having covalently linked amide bonds. Proteins comprise one or more amino acid polymer chains, generally known in the art as "polypeptides." "Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. "Synthetic peptides or polypeptides" refers to a non-naturally occurring peptide or polypeptide. Synthetic peptides or polypeptides can be synthesized, for example, using an automated polypeptide synthesizer. Various solid phase peptide synthesis methods are known to those of skill in the art. A protein may contain one or multiple polypeptides to form a single functioning biomolecule. A protein can include any of bio-therapeutic proteins, recombinant proteins used in research or therapy, trap proteins and other chimeric receptor Fc-fusion proteins, chimeric proteins, antibodies, monoclonal antibodies, polyclonal antibodies, human antibodies, and bispecific antibodies. Another exemplary aspect, a protein can include antibody fragments, nanobodies, recombinant antibody chimeras, cytokines, chemokines, peptide hormones, and the like. Proteins may be produced using recombinant cell-based production systems, such as the insect bacculovirus system, yeast systems (e.g., *Pichia* sp.), mammalian systems (e.g., CHO cells and CHO derivatives like CHO-K1 cells). For a recent review discussing biotherapeutic proteins and their production, see Ghaderi et al., "Production platforms for biotherapeutic glycoproteins. Occurrence, impact, and challenges of non-human sialylation," (Darius Ghaderi et al., *Production platforms for biotherapeutic glycoproteins. Occurrence, impact, and challenges of non-human sialylation,* 28 Biotechnology and Genetic Engineering Reviews 147-176 (2012)). In one aspect, proteins comprise modifications, adducts, and other covalently linked moieties. Those modifications, adducts and moieties include for example avidin, streptavidin, biotin, glycans (e.g., N-acetylgalactosamine, galactose, neuraminic acid, N-acetylglucosamine, fucose, mannose, and other monosaccharides), PEG, polyhistidine, FLAGtag, maltose binding protein (MBP), chitin binding protein (CBP), glutathione-S-transferase (GST) myc-epitope, fluorescent labels and other dyes, and the like. Proteins can be classified on the basis of compositions and solubility and can thus include simple proteins, such as, globular proteins and fibrous proteins; conjugated proteins, such as, nucleoproteins, glycoproteins, mucoproteins, chromoproteins, phosphoproteins, metalloproteins, and lipoproteins; and derived proteins, such as, primary derived proteins and secondary derived proteins. In one aspect, the protein of interest can be an antibody, a bispecific antibody, a multi-specific antibody, an antibody fragment, a monoclonal antibody, a fusion protein, or combinations thereof.

The term "antibody," as used herein includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, and FR4. In different embodiments of the invention, the FRs of the anti-big-ET-1 antibody (or antigen-binding portion thereof) may be identical to the human germline sequences or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

As used herein, an "antibody fragment" includes a portion of an intact antibody, such as, for example, the antigen-binding or variable region of an antibody. Examples of antibody fragments include, but are not limited to, a Fab fragment, a Fab' fragment, a F(ab')2 fragment, a scFv fragment, a Fv fragment, a dsFv diabody, a dAb fragment, a Fd' fragment, a Fd fragment, and an isolated complementarity determining region (CDR) region, as well as triabodies, tetrabodies, linear antibodies, single-chain antibody molecules, and multi specific antibodies formed from antibody fragments. Fv fragments are the combination of the variable regions of the immunoglobulin heavy and light chains, and ScFv proteins are recombinant single chain polypeptide molecules in which immunoglobulin light and heavy chain variable regions are connected by a peptide linker. In some exemplary embodiments, an antibody fragment contains sufficient amino acid sequence of the parent antibody of which it is a fragment that it binds to the same antigen as does the parent antibody; in some exemplary embodiments, a fragment binds to the antigen with a comparable affinity to that of the parent antibody and/or competes with the parent antibody for binding to the antigen. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains that are linked together, for example, by disulfide linkages. An antibody fragment may optionally comprise a multi-molecular complex. A functional antibody fragment typically comprises at least about 50 amino acids and more typically comprises at least about 200 amino acids.

The phrase "bispecific antibody" includes an antibody capable of selectively binding two or more epitopes. Bispecific antibodies generally comprise two different heavy chains, with each heavy chain specifically binding a different epitope—either on two different molecules (e.g., antigens) or on the same molecule (e.g., on the same antigen). If a bispecific antibody is capable of selectively binding two different epitopes (a first epitope and a second epitope), the affinity of the first heavy chain for the first epitope will generally be at least one to two or three or four orders of magnitude lower than the affinity of the first heavy chain for the second epitope, and vice versa. The epitopes recognized by the bispecific antibody can be on the same or a different target (e.g., on the same or a different protein). Bispecific antibodies can be made, for example, by combining heavy chains that recognize different epitopes of the same antigen. For example, nucleic acid sequences encoding heavy chain variable sequences that recognize different epitopes of the same antigen can be fused to nucleic acid sequences encoding different heavy chain constant regions, and such sequences can be expressed in a cell that expresses an immunoglobulin light chain.

A typical bispecific antibody has two heavy chains each having three heavy chain CDRs, followed by a $C_H1$ domain, a hinge, a $C_H2$ domain, and a $C_H3$ domain, and an immunoglobulin light chain that either does not confer antigen-binding specificity but that can associate with each heavy chain, or that can associate with each heavy chain and that can bind one or more of the epitopes bound by the heavy chain antigen-binding regions, or that can associate with each heavy chain and enable binding or one or both of the heavy chains to one or both epitopes. BsAbs can be divided into two major classes, those bearing an Fc region (IgG-like) and those lacking an Fc region, the latter normally being smaller than the IgG and IgG-like bispecific molecules comprising an Fc. The IgG-like bsAbs can have different formats, such as, but not limited to triomab, knobs into holes IgG (kih IgG), crossMab, orth-Fab IgG, Dual-variable domains Ig (DVD-Ig), Two-in-one or dual action Fab (DAF), IgG-single-chain Fv (IgG-scFv), or κλ-bodies. The non-IgG-like different formats include Tandem scFvs, Diabody format, Single-chain diabody, tandem diabodies (TandAbs), Dual-affinity retargeting molecule (DART), DART-Fc, nanobodies, or antibodies produced by the dock-and-lock (DNL) method (Gaowei Fan, Zujian Wang & Mingju Hao, *Bispecific antibodies and their applications,* 8 Journal of Hematology & Oncology 130; Dafne Müller & Roland E. Kontermann, *Bispecific Antibodies*, Handbook of Therapeutic Antibodies 265-310 (2014)).

The methods of producing bsAbs are not limited to quadroma technology based on the somatic fusion of two different hybridoma cell lines, chemical conjugation, which involves chemical cross-linkers, and genetic approaches utilizing recombinant DNA technology. Examples of bsAbs include those disclosed in the following patent applications, which are hereby incorporated herein by reference: U.S. Ser. No. 12/823,838, filed Jun. 25, 2010; U.S. Ser. No. 13/488,628, filed Jun. 5, 2012; U.S. Ser. No. 14/031,075, filed Sep. 19, 2013; U.S. Ser. No. 14/808,171, filed Jul. 24, 2015; U.S. Ser. No. 15/713,574, filed Sep. 22, 2017; U.S. Ser. No. 15/713,569, field Sep. 22, 2017; U.S. Ser. No. 15/386,453, filed Dec. 21, 2016; U.S. Ser. No. 15/386,443, filed Dec. 21, 2016; U.S. Ser. No. 15/22343 filed Jul. 29, 2016; and U.S. Ser. No. 15/814,095, filed Nov. 15, 2017. Low levels of homodimer impurities can be present at several steps during the manufacturing of bispecific antibodies. The detection of such homodimer impurities can be challenging when performed using intact mass analysis due to low abundances of the homodimer impurities and the co-elution of these impurities with main species when carried out using a regular liquid chromatographic method.

As used herein "multi-specific antibody" or "Mab" refers to an antibody with binding specificities for at least two different antigens. While such molecules normally will only bind two antigens (i.e. bispecific antibodies, bsAbs), antibodies with additional specificities such as trispecific antibody and KIH Trispecific can also be addressed by the system and method disclosed herein.

The term "monoclonal antibody" as used herein is not limited to antibodies produced through hybridoma technology. A monoclonal antibody can be derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof.

In some exemplary embodiments, the protein of interest can have a pI in the range of about 4.5 to about 9.0. In one aspect, the pI can be about 4.5, about 5.0, about 5.5, about 5.6, about 5.7, about 5.8, about 5.9, about 6.0, about 6.1 about 6.2, about 6.3, about 6.4, about 6.5, about 6.6, about 6.7, about 6.8, about 6.9, about 7.0, about 7.1 about 7.2, about 7.3, about 7.4, about 7.5, about 7.6, about 7.7, about 7.8, about 7.9, about 8.0, about 8.1 about 8.2, about 8.3, about 8.4, about 8.5, about 8.6, about 8.7, about 8.8, about 8.9, or about 9.0.

In some exemplary embodiments, the types of protein of interest in the sample matrix can be at least two. In one aspect, one of the at least two protein of interest can be a monoclonal antibody, a polyclonal antibody, a bispecific antibody, an antibody fragment, a fusion protein, or an antibody-drug complex. In some other embodiments, concentration of one of the at least two protein of interest can be about 20 mg/mL to about 400 mg/mL. In some exemplary embodiments, the types of protein of interest in the compositions are two. In some exemplary embodiments, the types of protein of interest in the compositions are three. In some exemplary embodiments, the types of protein of interest in the compositions are five.

In some exemplary embodiments, the two or more protein of interest in the composition can be selected from trap proteins, chimeric receptor Fc-fusion proteins, chimeric proteins, antibodies, monoclonal antibodies, polyclonal antibodies, human antibodies, bispecific antibodies, multi-specific antibodies, antibody fragments, nanobodies, recombinant antibody chimeras, cytokines, chemokines, or peptide hormones.

In some exemplary embodiments, the sample matrix can be a co-formulation.

In some exemplary embodiments, the protein of interest can be purified from mammalian cells. The mammalian cells can be of human origin or non-human origin can include primary epithelial cells (e.g., keratinocytes, cervical epithelial cells, bronchial epithelial cells, tracheal epithelial cells, kidney epithelial cells and retinal epithelial cells), established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LSI80 cells, LS174T cells, NCI-H-548 cells, RPMI2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PKi cells, PK(15) cells, GHi cells, GH3 cells, L2 cells, LLC-RC 256 cells, MHiCi cells, XC cells, MDOK cells, VSW cells, and TH-I, B1 cells, BSC-1 cells, RAf cells, RK-cells, PK-15 cells or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, Midi cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDMiC3 cells, KLN205 cells, McCoy cells, Mouse L cells, Strain 2071 (Mouse L) cells, L-M strain (Mouse L) cells, L-MTK' (Mouse L) cells, NCTC clones 2472 and 2555, SCC-PSA1 cells, Swiss/3T3 cells, Indian muntjac cells, SIRC cells, Cn cells, and Jensen cells, Sp2/0, NSO, NS1 cells or derivatives thereof).

In some exemplary embodiments, the method for characterizing a host-cell protein can comprise enriching host-cell proteins in the sample matrix by contacting the sample matrix with a chromatography support.

As used herein, the term "chromatography" refers to a process in which a chemical mixture carried by a liquid or gas can be separated into components as a result of differential distribution of the chemical entities as they flow around or over a stationary liquid or solid phase. Non-limiting examples of chromatography include traditional reversed phase (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Several types of liquid chromatography can be used with the mass spectrometer, such as, rapid resolution liquid chromatography (RRLC), ultra-performance liquid chromatography (UPLC), ultra-fast liquid chromatography (UFLC) and nano liquid chromatography (nLC). For further details on chromatography method and principles, see Colin et al. (COLIN F. POOLE ET AL., LIQUID CHROMATOGRAPHY FUNDAMENTALS AND INSTRUMENTATION (2017)).

In some exemplary embodiments, the chromatography support can be a liquid chromatography support. As used herein, the term "liquid chromatography" refers to a process in which a chemical mixture carried by a liquid can be separated into components as a result of differential distribution of the chemical entities as they flow around or over a stationary liquid or solid phase. Non-limiting examples of liquid chromatography include reversed phase liquid chromatography, ion-exchange chromatography, size exclusion chromatography, affinity chromatography, mixed-mode chromatography or hydrophobic chromatography.

As used herein, "ion exchange chromatography" can include separations including any method by which two substances are separated based on the difference in their respective ionic charges, either on the molecule of interest and/or chromatographic material as a whole or locally on specific regions of the molecule of interest and/or chromatographic material, and thus can employ either cationic exchange material or anionic exchange material. Ion exchange chromatography separates molecules based on differences between the local charges of the molecules of interest and the local charges of the chromatographic material. A packed ion-exchange chromatography column or an ion-exchange membrane device can be operated in a bind-elute mode, a flow-through, or a hybrid mode. After washing the column or the membrane device with the equilibration buffer or another buffer with different pH and/or conductivity, the product recovery can be achieved by increasing the ionic strength (e.g., conductivity) of the elution buffer to compete with the solute for the charged sites of the ion exchange matrix. Changing the pH and thereby altering the charge of the solute can be another way to achieve elution of the solute. The change in conductivity or pH may be gradual (gradient elution) or stepwise (step elution). The column can be then regenerated before next use. Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine (Q) groups. Cationic substituents include carboxymethyl (CM), sulfoethyl (SE), sulfopropyl (SP), phosphate (P) and sulfonate (S). Cellulose ion exchange medias or support can include DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow, and Capto™ S are all available from GE Healthcare. Further, both DEAE and CM derivatized ethylene glycol-methacrylate copolymer such as TOYOPEARL™ DEAE-650S or M and TOYOPEARL™ CM-650S or M are available from Toso Haas Co., Philadelphia, Pa., or Nuvia S and UNOSphere™ S from BioRad, Hercules, Calif, Eshmuno® S from EMD Millipore, MA.

As used herein, the term "hydrophobic interaction chromatography resin" can include a solid phase which can be covalently modified with phenyl, octyl, or butyl chemicals. It can use the properties of hydrophobicity to separate molecules from one another. In this type of chromatography, hydrophobic groups such as, phenyl, octyl, hexyl or butyl can be attached to the stationary column. Molecules that pass through the column that have hydrophobic amino acid side chains on their surfaces are able to interact with and bind to the hydrophobic groups on the column. Examples of hydrophobic interaction chromatography resins or support include Phenyl sepharose FF, Capto Phenyl (GE Healthcare, Uppsala, Sweden), Phenyl 650-M (Tosoh Bioscience, Tokyo, Japan) and Sartobind Phenyl (Sartorius corporation, New York, USA).

As used herein, the term "Mixed Mode Chromatography (MMC)" or "multimodal chromatography" includes a chromatographic method in which solutes interact with stationary phase through more than one interaction mode or mechanism. MMC can be used as an alternative or complementary tool to traditional reversed phase (RP), ion exchange (IEX) and normal phase chromatography (NP). Unlike RP, NP and IEX chromatography, in which hydrophobic interaction, hydrophilic interaction and ionic interaction respectively are the dominant interaction modes, mixed-mode chromatography can employ a combination of two or more of these interaction modes. Mixed mode chromatography media can provide unique selectivity that cannot be reproduced by single mode chromatography. Mixed mode chromatography can also provide potential cost savings, longer column lifetimes and operation flexibility compared to affinity-based methods. In some exemplary embodiments, the mixed mode chromatography media can be comprised of mixed mode ligands coupled to an organic or inorganic support, sometimes denoted a base matrix, directly or via a spacer. The support may be in the form of particles, such as essentially spherical particles, a monolith, filter, membrane, surface, capillaries, etc. In some specific exemplary embodiments, the support can be prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (Stellan Hjertén, *The preparation of agarose spheres for chromatography of molecules and particles,* 79 Biochimica et Biophysica Acta (BBA)—Biophysics including Photosynthesis 393-398 (1964) incorporated herein by reference). Alternatively, the support can be prepared from a synthetic polymer, such as cross-linked synthetic polymers, e.g., styrene or styrene derivatives, divinylbenzene, acrylamides, acrylate esters, methacrylate esters, vinyl esters, vinyl amides etc. Such synthetic polymers can be produced according to standard methods, see e.g., Eduardo Vivaldo-Lima et al., *An Updated Review on Suspension Polymerization,* 36 Industrial & Engineering Chemistry Research 939-965 (1997). Porous native or synthetic polymer supports are also available from commercial sources, such as Amersham Biosciences, Uppsala, Sweden.

In some exemplary embodiments, the method for characterizing a host-cell protein can comprise enriching host-cell proteins in the sample matrix by contacting the sample matrix with an affinity chromatography support.

As used herein, "affinity chromatography" can include separations including any method by which two substances are separated based on their affinity to a chromatographic material. Non-limiting examples of affinity chromatography support include, but are not limited to Protein A resin, Protein G resin, affinity supports comprising the antigen against which the binding molecule was raised, and affinity supports comprising an Fc binding protein. The affinity chromatography resin can be formed by immobilizing Protein A, Protein G, antigen against which the binding molecule was raised, or Fc binding protein on a resin, such as, agarose or sepharose. There are several commercial sources for Protein A resin. Non-limiting examples of Protein A resin include Mab Select SuRe™, Mab Select SuRe LX, MabSelect, Mab Select Xtra, rProtein A Sepharose from GE Healthcare, and ProSep HC, ProSep Ultra, and ProSep Ultra Plus from EMD Millipore.

In one aspect, the affinity chromatographic material can be equilibrated with a suitable buffer prior to sample matrix loading. Following this equilibration, the sample matrix can be loaded onto the column. In one aspect, following the loading of the affinity chromatographic material, the affinity chromatographic material can be washed one or multiple times using an appropriate wash buffer. In some specific aspects, a flow-through from the wash can be collected. In some specific aspects, the flow-through from the wash can be further processed. Optionally other washes, including washes employing different buffers, can be employed prior to eluting the column. A flow-through from the washes can be collected and further processed. The affinity chromatographic material can also be eluted using an appropriate elution buffer. The eluate can be monitored using techniques well known to those skilled in the art. For example, the absorbance at OD280 can be followed. The elution fraction (s) of interest can then be prepared for further processing.

In one aspect, a kosmotropic salt solution can be supplemented into the sample matrix comprising the protein of interest prior to contacting with an affinity chromatography resin. The kosmotropic salt solution comprises at least one kosmotropic salt. Examples of suitable kosmotropic salts include, but are not limited to ammonium sulfate, sodium sulfate, sodium citrate, potassium sulfate, potassium phosphate, sodium phosphate and a combination thereof. In one aspect, the kosmotropic salt is ammonium sulfate; in another aspect, the kosmotropic salt is sodium sulfate; and in another aspect, the kosmotropic salt is sodium citrate. The kosmotropic salt is present in the kosmotropic salt solution at a concentration of from about 0.3 M to about 1.1 M. In one embodiment, the kosmotropic salt is present in the kosmotropic salt solution at a concentration of about 0.5 M.

In some exemplary embodiments, the enrichment step can further comprise treating a sample obtained from the chromatography support.

In some exemplary embodiments, the treatment can include adding a digestion agent to the sample to produce peptides. As used herein, the term "digestion agent" refers to any one or combination of a large number of different agents that can perform digestion of a protein. Non-limiting examples of hydrolyzing agents that can carry out enzymatic digestion include trypsin, endoproteinase Arg-C, endoproteinase Asp-N, endoproteinase Glu-C, outer membrane protease T (OmpT), immunoglobulin-degrading enzyme of *Streptococcus pyogenes* (IdeS), chymotrypsin, pepsin, thermolysin, papain, pronase, and protease from *Aspergillus Saitoi*. Non-limiting examples of hydrolyzing agents that can carry out non-enzymatic digestion include the use of high temperature, microwave, ultrasound, high pressure, infrared, solvents (non-limiting examples are ethanol and acetonitrile), immobilized enzyme digestion (IMER), magnetic particle immobilized enzymes, and on-chip immobilized enzymes. For a recent review discussing the available techniques for protein digestion see Switazar et al., "Protein Digestion: An Overview of the Available Techniques and Recent Developments" (Linda Switzar, Martin Giera & Wilfried M. A. Niessen, *Protein Digestion: An Overview of the Available Techniques and Recent Developments,* 12 Journal of Proteome Research 1067-1077 (2013)). One or a combination of hydrolyzing agents can cleave peptide bonds in a protein or polypeptide, in a sequence-specific manner, generating a predictable collection of shorter peptides.

The term ratio of hydrolyzing agent to the protein and the time required for digestion can be appropriately selected to obtain a digestion of the protein. When the enzyme to substrate ratio is unsuitably high, it can cause a non-specific cleavage (potentially breaking all proteins/peptides into individual amino acids) thereby limiting the ability to identify proteins as well as reducing sequence coverage. On the other hand, a low E/S ratio would need long digestion and thus long sample preparation time. The enzyme to substrate ratio can range from about 1:0.5 to about 1:500.

As used herein, the term "digestion" refers to hydrolysis of one or more peptide bonds of a protein. There are several approaches to carrying out digestion of a protein in a sample using an appropriate hydrolyzing agent, for example, enzymatic digestion or non-enzymatic digestion.

One of the widely accepted methods for digestion of proteins in a sample involves the use of proteases. Many proteases are available and each of them have their own characteristics in terms of specificity, efficiency, and optimum digestion conditions. Proteases refer to both endopeptidases and exopeptidases, as classified based on the ability of the protease to cleave at non-terminal or terminal amino acids within a peptide. Alternatively, proteases also refer to the six distinct classes—aspartic, glutamic, and metalloproteases, cysteine, serine, and threonine proteases, as classified on the mechanism of catalysis. The terms "protease" and "peptidase are used interchangeably to refer to enzymes which hydrolyze peptide bonds."

Apart from contacting a host-cell protein to a hydrolyzing agent, the method can optionally include steps for reducing the host-cell protein, alkylating the host-cell protein, buffering the host-cell protein, and/or desalting the sample matrix. These steps can be accomplished in any suitable manner as desired.

In some exemplary embodiments, the treatment can include adding a protein reducing agent to the sample. As used herein, the term "protein reducing agent" refers to the agent used for reduction of disulfide bridges in a protein. Non-limiting examples of the protein reducing agents used to reduce the protein are dithiothreitol (DTT), ß-mercaptoethanol, Ellman's reagent, hydroxylamine hydrochloride, sodium cyanoborohydride, tris(2-carboxyethyl)phosphine hydrochloride (TCEP-HCl), or combinations thereof.

In some exemplary embodiments, the treatment can include adding a protein alkylating agent to the sample. As used herein, the term "protein alkylating agent" refers to the agent used for alkylate certain free amino acid residues in a protein. Non-limiting examples of the protein alkylating agents are iodoacetamide (IOA), chloroacetamide (CAA), acrylamide (AA), N-ethylmaleimide (NEM), methyl methanethiosulfonate (MMTS), and 4-vinylpyridine or combinations thereof.

In some exemplary embodiments, the treatment can include adding one or more from the group consisting of alkylating agent, reducing agent, hydrolyzing agent or combinations thereof. The additions of these agents to the sample can vary. The addition can be carried out by adding the sample to the agents or by adding the agents to the samples.

As used herein, the term "mass spectrometer" includes a device capable of identifying specific molecular species and measuring their accurate masses. The term is meant to include any molecular detector into which a polypeptide or peptide may be eluted for detection and/or characterization. A mass spectrometer can include three major parts: the ion source, the mass analyzer, and the detector. The role of the ion source is to create gas phase ions. Analyte atoms, molecules, or clusters can be transferred into gas phase and ionized either concurrently (as in electrospray ionization) or through separate processes. The choice of ion source depends heavily on the application.

In some exemplary embodiments, the mass spectrometer can be a tandem mass spectrometer.

As used herein, the term "tandem mass spectrometry" includes a technique where structural information on sample matrix molecules is obtained by using multiple stages of mass selection and mass separation. A prerequisite is that the sample matrix molecules can be transferred into the gas phase and ionized intact and that they can be induced to fall apart in some predictable and controllable fashion after the first mass selection step. Multistage MS/MS, or $MS^n$, can be performed by first selecting and isolating a precursor ion ($MS^2$), fragmenting it, isolating a primary fragment ion ($MS^3$), fragmenting it, isolating a secondary fragment ($MS^4$), and so on as long as one can obtain meaningful information or the fragment ion signal is detectable. Tandem MS has been successfully performed with a wide variety of analyzer combinations. What analyzers to combine for a certain application can be determined by many different factors, such as sensitivity, selectivity, and speed, but also size, cost, and availability. The two major categories of tandem MS methods are tandem-in-space and tandem-in-time, but there are also hybrids where tandem-in-time analyzers are coupled in space or with tandem-in-space analyzers. A tandem-in-space mass spectrometer comprises an ion source, a precursor ion activation device, and at least two non-trapping mass analyzers. Specific m/z separation functions can be designed so that in one section of the instrument ions are selected, dissociated in an intermediate region, and the product ions are then transmitted to another analyzer for m/z separation and data acquisition. In tandem-in-time, mass spectrometer ions produced in the ion source can be trapped, isolated, fragmented, and m/z separated in the same physical device.

The peptides identified by the mass spectrometer can be used as surrogate representatives of the intact protein and their post translational modifications. They can be used for protein characterization by correlating experimental and theoretical MS/MS data, the latter generated from possible peptides in a protein sequence database. The characterization includes, but is not limited to, sequencing amino acids of the protein fragments, determining protein sequencing, determining protein de novo sequencing, locating post-translational modifications, or identifying post translational modifications, or comparability analysis, or combinations thereof.

As used herein, the term "Multiple reaction monitoring" or "MRM" refers to a targeted protein characterization method that encompass three quadrupoles (QQQ) for enhanced sensitivity and selectivity on a triple quadrupole mass spectrometer. The first quadrupole (Q1) is set to only allow the predefined m/z value of the precursor ion to pass into the second quadrupole, or the collision cell. In the collision cell, the selected ions enter a higher pressure region with argon or nitrogen gas, resulting in low energy collisions and fragmentation of the selected precursor ion into many product ions. Finally, only the preselected product ions with specific m/z values are allowed to pass through the third quadrupole (Q3) and on to the detector. The result is a very selective means for separating the target ions away from everything that is being introduced into the mass spectrometer (e.g., through liquid chromatography or other sample introduction), and further detecting fragment ions of the target and reducing chemical noise from the sample. In context of MRM, the lower limit of quantification refers to the lowest concentration of the analyte (protein) at which quantitative measurements can be made.

As used herein, the term "database" refers to bioinformatic tools which provide the possibility of searching the uninterpreted MS-MS spectra against all possible sequences in the database(s). Non-limiting examples of such tools are Mascot (http://www.matrixscience.com), Spectrum Mill (http://www.chem.agilent.com), PLGS (http://www.waters-.com), PEAKS (http://www.bioinformaticssolutions.com), Proteinpilot (http://download.appliedbiosystems.com//proteinpilot), Phenyx (http://www.phenyx-ms.com), Sorcerer (http://www.sagenresearch.com), OMSSA (http://www.pubchem.ncbi.nlm.nih.gov/omssa/), X!Tandem (http://www.thegpm.org/TANDEM/), Protein Prospector (http://www. http://prospector.ucsf.edu/prospector/mshome.htm), Byonic (https://www.proteinmetrics.com/products/byonic), Andromeda (https://www.ncbi.nlm.nih.gov/pubmed/21254760) or Sequest (http://fields.scripps.edu/sequest).

In some exemplary embodiments, the mass spectrometer can be coupled to a liquid chromatography system. In another exemplary embodiment, the mass spectrometer can be coupled to a nano liquid chromatography. In one aspect, the mobile phase used to elute the protein in liquid chromatography can be a mobile phase that can be compatible with a mass spectrometer. In a specific aspect, the mobile phase can be ammonium acetate, ammonium bicarbonate, or ammonium formate, acetonitrile, water, formic acid, a volatile acid, or combinations thereof.

As used herein, the "non-denaturing digestion conditions" or "native conditions" can include conditions that do not cause protein denaturation. Protein denaturing can refer to a process in which the three-dimensional shape of a molecule is changed from its native state without rupture of peptide bonds. The protein denaturation can be carried out using a protein denaturing agent, such as chaotropic agents. Chaotropic solutes increase the entropy of the system by interfering with intramolecular interactions mediated by non-covalent forces such as hydrogen bonds, van der Waals forces, and hydrophobic effects. Non-limiting examples for non-denaturing conditions include water or buffers. The water used can be distilled and/or deionized. In some exemplary embodiments, the solvents can be HPLC grade. Non-limiting examples of buffers can include ammonium acetate, tris-hydrochloride, ammonium bicarbonate, ammonium formate, or combinations thereof. In one aspect, the concentration of the buffer can be at most 1 M. The native conditions can also include use of digestion agent in an amount such that only the protein of interest can get digested and said host cell protein stays in the native form.

It is understood that the methods are not limited to any of the aforesaid protein, host-cell protein, chromatography support, mass spectrometry, digestion method and that the methods for characterizing host-cell proteins may be conducted by any suitable means.

The consecutive labeling of method steps as provided herein with numbers and/or letters is not meant to limit the method or any embodiments thereof to the particular indicated order.

Various publications, including patents, patent applications, published patent applications, accession numbers, technical articles and scholarly articles are cited throughout the specification. Each of these cited references is incorporated by reference, in its entirety and for all purposes, herein.

The present invention will be more fully understood by reference to the following Examples. They should not, however, be construed as limiting the scope of the invention

EXAMPLES

Materials. Recombinant liver carboxylesterase 1-like (CES-1L) protein was custom ordered from Genscript Biotech (Piscataway, NJ). Anti-CES1 rabbit polyclonal antibody was purchased from MyBiosource (San Diego, CA). Tris-HCl, dithiothreitol (DTT), iodoacetamide (IAM), and formic acid (FA) were from Thermo Fisher Scientific (Waltham, MA). Sequencing grade modified trypsin was from Promega (Madison, WI). Centrifugal filters, NanoSep 10 kDa Omega spin filter from Pall (USA) and 3K Amicon ultra centrifugal filter from Milipore Sigma (USA) were purchased. LC/MS grade acetonitrile with 0.1% FA and water with 0.1% FA were from Fisher Scientific (USA). Zorbax RRHD Eclipse Plus C18 column was from Agilent (USA). Mili-Q water used in the experiment was provided in-house. The DS-a mAb was used as assay matrix, and final concentrated pool (FCP) and DS materials of mAbs were produced at Regeneron.

Native Digestion for HCP Profiling

The native digestion concept was adapted from a previously published approach with further optimization (Huang et al., A Novel Sample Preparation for Shotgun Proteomics Characterization of HCPs in Antibodies, Analytical Chemistry 89(10) (2017); Molden et al., Host cell protein profiling of commercial therapeutic protein drugs as a benchmark for monoclonal antibody-based therapeutic protein development, mAbs 13(1) (2021)). FCP/DS samples were buffer exchanged to water using 3K Amicon centrifugal filters prior to native digestion. The concentration of each buffer exchanged sample was measured by nanodrop, and 2 mg of mAb was used in the digestion process. Internal standards were spiked into the mAb, and 0.4 μg of reconstituted trypsin solution was added to digest the samples overnight at 37° C. with shaking. After digestion, 3.5 mM dithiothreitol (DTT) was added to mixtures and incubated at 90° C. for 20 minutes to reduce the disulfide bonds. The reduced mixtures were alkylated by adding 5.2 mM IAM and incubated in the dark for 30 minutes at room temperature. Next, the precipitated protein mixtures were centrifuged, and the supernatant was filtered by a 10 kDa Nanosep filter. The collected solution was acidified with 10% FA prior to LC-MS analysis.

Preparation of Calibration Standards

A CES-free mAb (DS-a) was prepared at 10 and 20 mg/mL and used as the assay matrix. 1250 ppm stock solution was prepared by spiking 1250 ng of recombinant CES into 1 mg of 10 or 20 mg/mL mAb. The 1250-ppm stock was serially diluted at 2.5-fold with matrix to generate calibration standards at 0.05, 0.13, 0.33, 0.82, 2.05, 5.12, 12.8, 32, 80, 200, and 500 ppm.

Direct Digestion

20 μL of calibration standards (in 10 mg/mL matrix), samples and controls were transferred to a 96 well plate and concentrated to dryness using a sample concentrator. Then the dried proteins were reconstituted in the denaturation and reduction solution (8 M Urea, 10 mM TCEP-HCl) with brief mixing and incubated at 56° C. with shaking for 30 minutes. After cooling down, 10 mM of IAM was added, and mixtures were incubated at room temperature in the dark for 30 minutes for alkylation reaction. Following alkylation, 10 μg of trypsin in large volume was added to the mixture (1:20 of trypsin to substrate ratio) and incubated at 37° C. for 4 hours with shaking. At the end of digestion, 10% FA was added to quench the reaction.

Native Digestion for MRM Quantitation

Native digestion experiment of CES calibration standards (in 20 mg/mL or 10 mg/mL), samples and controls was performed for MRM quantitation following the same procedure described above (see native digestion for HCP profiling).

LC-MS/MS Analysis

50 μL of supernatant from native digestion was injected into a Waters ACQUITY I-Class UPLC system coupled to a Thermo Scientific Q Exactive Plus Orbitrap MS. The UPLC system was equipped with a Waters ACQUITY Peptide CSH C18 column (130 Å, 1.7 μm particle size, 2.1 mm×150 mm). 0.1% FA in water and 0.1% FA in acetonitrile were used as mobile phase A and mobile phase B, respectively. An elution gradient starting at 0.1% B for 5 min then ramped to 40% B over 85 min at a flow rate of 0.25 mL/min. The mass spectrometry data acquisition was operated in a data dependent mode (DDA). In the full MS settings, 70,000 resolution, 1e6 AGC target and 500 ms injection time were used. For data dependent $MS^2$ settings, 17,500 resolution, 1e5 AGC target and 100 ms injection time were applied. Each full MS scan was followed by ten data dependent $MS^2$ scans with 30 s dynamic exclusion duration.

LC-MS/MS-MRM

Half of the digested sample was injected into the LC-MS system using an Agilent 1290 Infinity II LC System with Agilent Zorbax RRHD Eclipse Plus C18 column (2.1×50 mm, 1.8 μm, 95 Å) for reverse-phase chromatography. 0.1% FA in water and 0.1% FA in acetonitrile were used as mobile phase A and mobile phase B, respectively. The initial gradient started at 0.1% B for 0.5 min then increased to 40% B over 20 min followed by 90% B wash and 0.1% B equilibration for 5 min. Flow rate of 0.4 mL/min was used in the gradient. Agilent 6495C Triple Quadrupole mass spectrometer (MS) with Agilent Jet Stream electrospray ionization (AJS ESI) source was used to perform MRM analysis. The AJS ESI source was applied with heated nitrogen as sheath gas and drying gas at 400° C. and 180° C., respectively, at a flow rate of 12 L/min. The MS was operated at positive mode with capillary at 3000 V and nozzle voltage at 300 V and nebulizer at 35 psi. Acquisition of the pre-selected transitions of precursor and product ion pair were split into multiple time segments during elution gradient (0-7.79 min; 7.8-9.79 min; 9.8-20.0 min). Unit mass resolution (0.7 FWHM) was chosen for both MS1 and MS2 quadrupoles.

Data Processing

For HCP profiling, the collected MS spectra was searched against *Cricetulus griseus* reference proteome downloaded from Uniprot using Byonic software from PMI. Precursor mass and fragment mass tolerance was set to 20 ppm. Trypsin was set as the digestion enzyme and allowed up to 2 missed cleavages. Peptide modifications were set for methionine oxidation as a common variable and cysteine alkylation as fixed modifications. 2% of protein false discovery rate was set as the level of confidence for protein identification. The open-source Skyline software was used for further data processing.

The raw data collected from LC-MS/MS-MRM experiments were analyzed using Agilent MassHunter Workstation Quantitative Analysis, version 10.1.

Example 1

LC-MS/MS Workflow for HCP Identification and Quantification

The HCP analysis strategy is illustrated in FIG. 1. HCP identification and semi-quantification were performed by native digestion and UPLC-MS in DDA mode. The profiling workflow has sufficient throughput to support the process development and high sensitivity (1-2 ppm) to detect residual HCPs in the purified drug candidates. To monitor certain specific high-risk HCP, MRM method was developed and applied. Direct digestion coupled with targeted MS method is capable of quantifying HCPs at 1 ppm, and this strategy can be utilized to monitor several high-risk HCPs. LC-MRM method with sub-ppm sensitivity may be required to monitor the potential problematic HCPs.

Example 2

HCPs Profiling by Native Digestion

HCP profiling by LC-MS was performed for three mAbs (mAb1, mAb2, and mAb3) that were produced in-house. The MS-based native digestion method was applied for HCP identification and semi-quantification in these antibodies generated by two different processes. Identification of low abundant HCPs in DS is challenging due to poor MS/MS fragmentation and low-intensity peaks buried in chromatographic noise. An MS/MS fragmentation library of HCPs collected from early downstream purification process samples (e.g., affinity capture pool) was applied to facilitate HCP identification in DS. The HCP analysis was performed on UPLC-MS, which enables reproducible retention time among different instruments and multiple experiment replicates. Therefore, the retention time of HCPs library was also utilized for the assignment of low-intensity peaks in DS. The identified HCP abundances were calculated by dividing the top two to three unique peptides of HCP against spiked standards.

There were 23 HCPs identified from all antibodies. HCP abundances were higher in mAb1 compared to mAb2 and mAb3 (FIG. 2). In mAb1, the top five most abundant HCPs were peroxiredoxin-1 (64-97 ppm), CES-1L protein (10-43 ppm), TIMP1 (21-23 ppm), U4/U6 small nuclear ribonucleoprotein Prp4 (17-23 ppm), and putative PLBD2 (10-19 ppm). The rest of the HCPs were below 12 ppm in mAb1. In mAb2 and mAb3, the majority of HCPs identified were at low levels (<10 ppm).

Several potential high-risk HCPs with lipase/esterase or protease activities were identified from mAb1. These HCPs present at higher levels in mAb1, but are not detected in mAb2 and mAb3. Particularly, a serine esterase, CES-1L, was detected at about 40 ppm in the DS of mAb1 generated by process 1. A total of 14 peptides from CES protein were identified from mAb1 with high MS/MS quality (results not shown), which provides confident identification of this HCP. A majority of the peptides were widely shared in multiple CES isoforms (CES-1L, CES-B1L (liver carboxylesterase B-1-like) and CES4 (liver carboxylesterase 4)).

It was the first time this esterase HCP was observed at such high levels in the DS by LC-MS approaches. There was no stability or product quality issue discovered during process development in the DS of mAb1, mAb2 and mAb3, which were manufactured in histidine and sucrose-containing excipient buffer. However, some initial trends of instability were shown in the formulated DS (FDS) of mAb1, which added polysorbate 80 (PS80) as an excipient. Visible particle formation was observed in mAb1 FDS upon agitation and thermal stress stability tests. Thus, further investigations were triggered to evaluate the effect of PS80 on the stability of mAb1. Under incubation of FDS at 5° C. for 25 days, 30% of PS80 was lost in mAb1, whereas not in mAb2 and mAb3. Therefore, PS80 degradation leads to the particulates in mAb1. The ABPP-based strategy was further utilized to enrich HCPs with esterase activity that can degrade PS80 (Zhang et al., Rapid Polysorbate 80 Degradation by Liver Carboxylesterase in a Monoclonal Antibody Formulated Drug Substance at Early Stage Development, Journal of Pharmaceutical Sciences 109(11) (2020)). CES-B1L and CES-1L were detected by the ABPP approach using a serine hydrolase probe. No PS80 degradation was observed in mAb1 after depleting CES-B1L and CES-1L, thus confirming CES is responsible for the PS80 degradation as previously reported (Zhang et al., supra).

Figure 3:
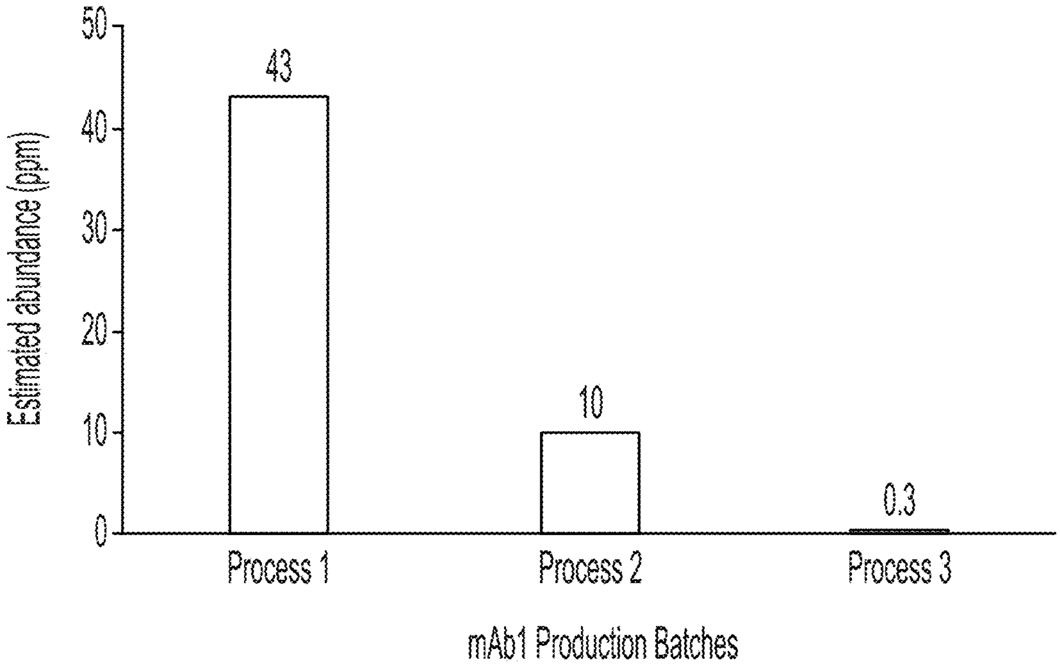
FIG. 3 shows an estimated abundance (in ppm) of Liver carboxylesterase levels determined by native digestion in mAb1 from different purification processes according to an exemplary embodiment.

In the early stage of drug development, a generic purification platform (process 1 and process 2) with minimal optimization was utilized. Upon discovering the CES and correlating the activity with PS80 degradation, major efforts have also been made to improve the purification process to remove CES from mAb1. New purification platforms and strategies were assessed during the process development of mAb1. Under the product specific and optimized purification conditions (process 3), the overall HCP content has been decreased (data not shown), and the abundance of CES has been significantly reduced to below one ppm in one batch of DS produced from process 3 (FIG. 3). CES is a highly active lipase and has shown activity at a sub-ppm level from ABPP study (Zhang et al., supra). Therefore, an absolute quantitation assay with high sensitivity is necessary to accurately measure this problematic HCP and ensure the process consistency in mAb1.

Protein samples were dried down and resuspended in DPBS. rProtein A Sepharose was packed in columns and equilibrated with 5 column volumes of DPBS, pH 8.4. The protein sample was pipetted onto each column and incubated for 4 minutes at room temperature. The HCP flowthrough was collected and saved. Each column was washed with 3 column volumes of DPBS, pH 8.4 and the HCP eluate was combined with the flow-through. Collected HCP eluates were buffer exchanged into 50 mM ammonium acetate.

Example 3

Surrogate Peptide Selection and Standard Characterization for MRM Assay Development Recombinant CES-1L protein expressed from *Escherichia coli* was used as the surrogate protein in the MRM assay. The molecular weight of the CES is confirmed by intact mass analysis, and 100% amino acid sequence coverage of the recombinant protein was achieved from the peptide mapping analysis (data not shown).

A suitable surrogate peptide should have a high MS signal, no mis-cleavage and post-translational modification sites. Ideally, the surrogate peptide should be a unique peptide with an appropriate length. Identified in mAb1 samples, several CES isoforms are presented with shared sequences. Most of the peptides were found to belong to two isoforms: CES-B1L (Uniprot accession#: A0A061I7X9, A0A061I6Q8, A0A061IAA7) and CES-1L (Uniprot accession#: A0A061IFE2). Some of the peptides were also shared in other isoforms, CES1, CES4, and carboxylic ester hydrolase, but lesser compared to the 'B-1-like' and '1-like' isoforms.

Additionally, more than one Uniprot accession number was reported for these isoforms (except CES-1L). The protein sequence of CES-B1L isoforms was highly similar and partially overlapped with the '1-like' isoform. Based on the identified peptides in mAb1, it was challenging to differentiate each isoform. Therefore, peptides belonging to 'B-1-like' and '1-like' isoforms (MAIALLQK) and common to all isoforms (APEEILAEK and NFNTVPYIVGINK) were selected for targeted quantitation (Table 1). The MRM transition and collision energy were optimized for each peptide to maximize the assay sensitivity (Table 1). Assay matrix selection is critical in MRM method development that it should mimic the sample matrix as close as possible and has no or minimal endogenous interference. Several in-house produced mAbs were evaluated (data not shown), and DS-a was selected as the assay matrix as it showed the lowest background interference. The DS-a digestion exhibited no interference at the peptide retention times of MAIALLQK and NFNTVPYIVGINK, but showed some background signals with APEEILAEK. Thus, the APEEILAEK peptide was not selected for quantitation as the interference may impact assay accuracy.

TABLE 1

Optimized Transition and Collision Energy used in the MRM Quantitation Method

| Protein | Peptide Sequence | MRM transition | Collision Energy (V) |
|---|---|---|---|
| Liver carboxylesterase B-1-like, Liver carboxylesterase 1-like | MAIALLQK | 444.3 (+2) > 685.5 (+1) | 12 |
| Liver carboxylesterase B-1-like, Liver carboxylesterase 1-like, Liver carboxylesterase 1, Liver carboxylesterase 4, Carboxylic ester hydrolase | NFNTVPYIVGINK | 739.9 (+2) > 903.5 (+1) | 23 |
| Liver carboxylesterase B-1-like, Liver carboxylesterase 1-like, Liver carboxylesterase 1, Liver carboxylesterase 4, Carboxylic ester hydrolase | APEEILAEK | 500.3 (+2) > 464.8 (+2) | 18 |

Example 4

Direct Digestion MRM Method Development

Figure 4A:
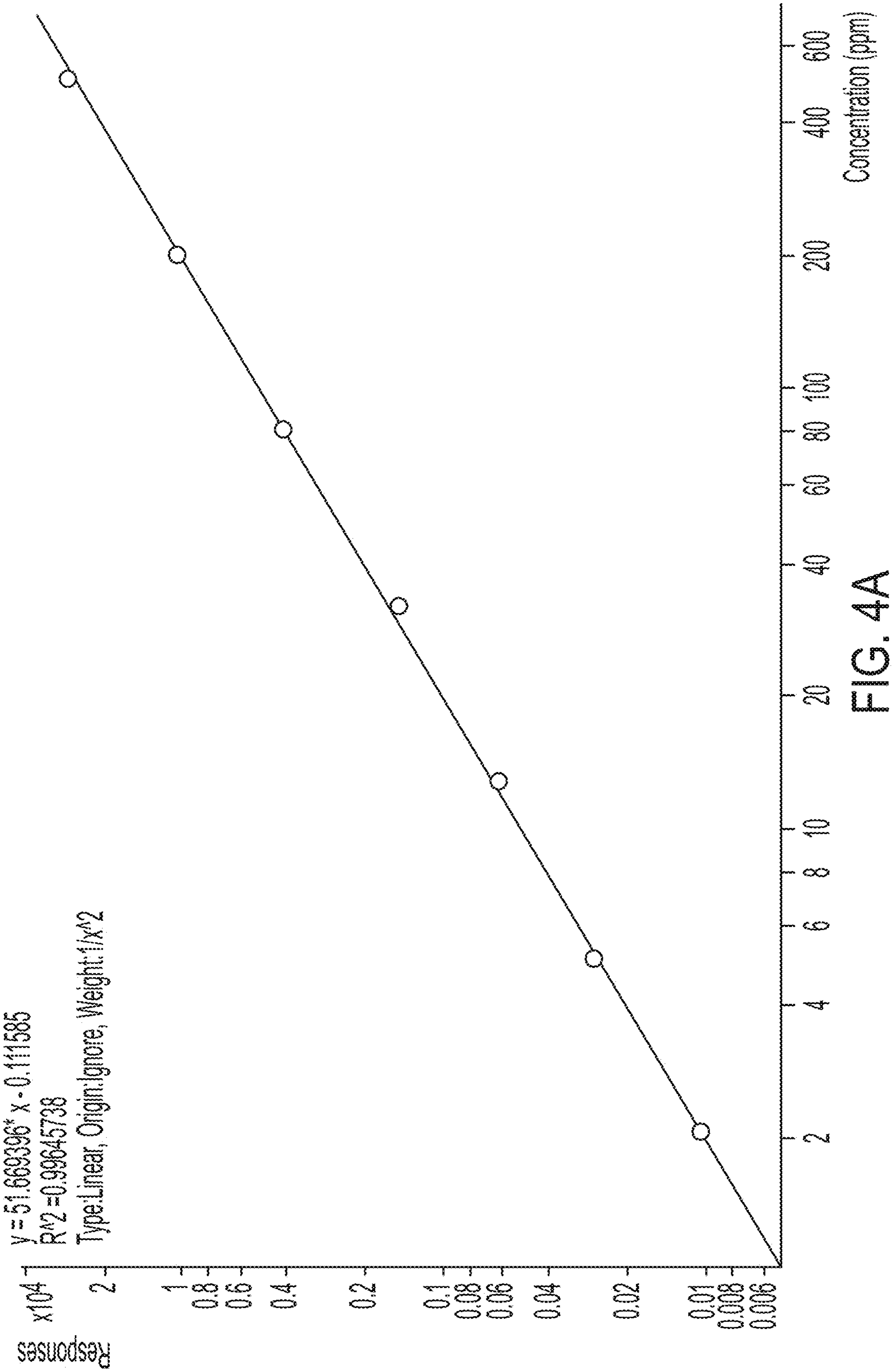
FIG. 4A shows a standard curve for APEEILAEK ranged from 2-500 ppm from direct digestion, the linear regression and R square according to an exemplary embodiment.
Figure 4B:
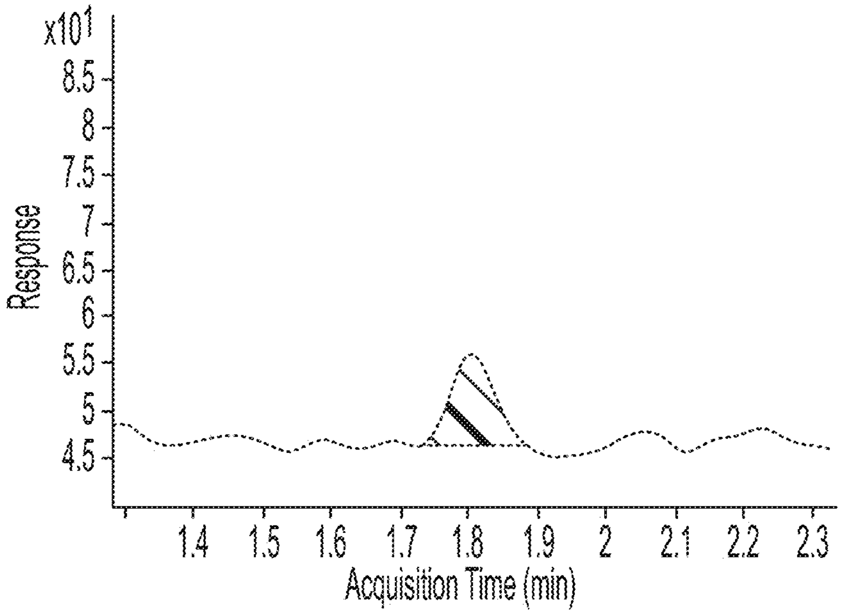
FIG. 4B shows an extracted ion chromatograms (EIC) of APEEILAEK at 0.8 ppm according to an exemplary embodiment.
Figure 4C:
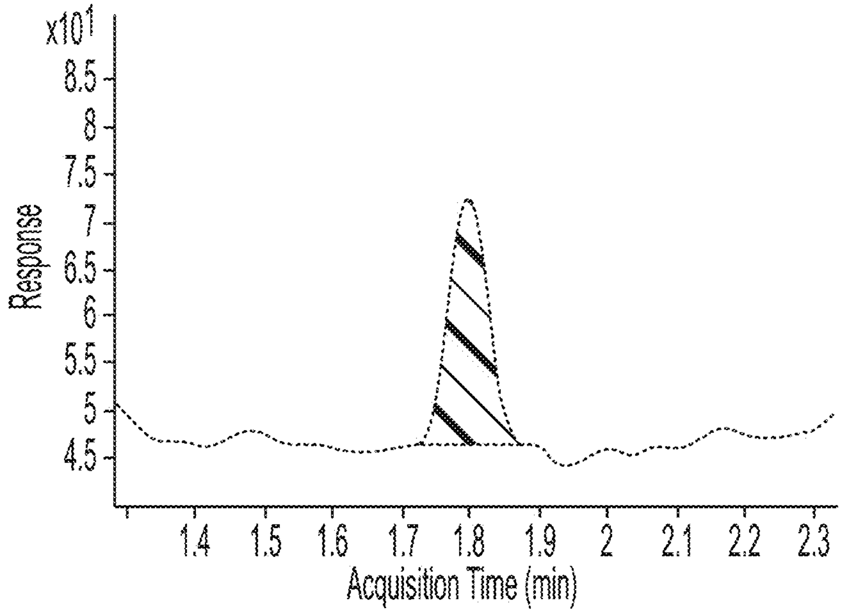
FIG. 4C shows an extracted ion chromatograms (EIC) of APEEILAEK at 2 ppm according to an exemplary embodiment.

Initially, direct digestion preparation coupled with MRM was performed to estimate the CES levels in DS. In the direct digestion method, the calibration standard in the assay matrix and samples were digested using trypsin. The entire peptides pool was injected into the analytical LC-triple quadrupole MS setup. A linear curve ranging from 2-500 ppm with $R^2$ above 0.99 was achieved in the direct-MRM approach (FIG. 4*a*). The extracted ion chromatograms of the analyte at limit of detection (LOD; 0.8 ppm) and lower limit of quantitation (LLOQ; 2.0 ppm) both showed distinct peak integration (FIGS. 4*b* and 4*c*). The sensitivity was comparable to several recently reported MRM methods for lipase quantitation (Gao et al., Targeted Host Cell Protein Quantification by LC-MRM Enables Biologics Processing and Product Characterization, Analytical Chemistry 92 (2020); Chena et al., A Highly Sensitive LC-MS/MS Method for Targeted Quantitation of Lipase Host Cell Proteins in Biotherapeutics, Pharmaceutical Biotechnology 110 (2021)). However, the LLOQ was relatively high for CES quantification by direct digestion, as lipase activity was observed at a sub-ppm level. Thus, a higher sensitivity MRM quantification method was required for monitoring the CES levels to support process development.

Example 5

Affinity Depletion MRM Method Development

The MRM method sensitivity can be improved by implementing an HCP enrichment strategy or DS depletion strategy. An affinity enrichment method, which specifically captures CES-1L protein, was evaluated. However, this method suffered from low recovery and poor linearity (data not shown). Moreover, the LLOQ (5 ppm) of the affinity depletion method was higher than the direct digestion method. The poor performance of the affinity enrichment method may be mainly attributed to the anti-human CES1 polyclonal antibody utilized to enrich CES. A specific anti-CHO HCP antibody may be required to improve the sensitivity of the affinity enrichment strategy. A similar affinity depletion MRM strategy was reported (Gao et al., supra) in a previous publication and no significant sensitivity improvement was observed compared to direct digestion.

Example 6

Native Digestion MRM Method Development

The native digestion offers a simple and robust method for HCP detection in antibodies (Huang et al., A Novel Sample Preparation for Shotgun Proteomics Characterization of HCPs in Antibodies, Analytical Chemistry 89(10) (2017)). Under native conditions, HCPs were selectively digested by enzymes whereas the antibodies were minimally digested and further precipitated and removed. This method offers 1-2 ppm sensitivity by regular LC-MS/MS experiment for HCPs detection and has been frequently applied to support antibody purification process development in the industry. However, implementing native digestion to MRM workflow has not been widely evaluated. Here, we evaluated the sensitivity of absolute quantification when coupling to native digestion to deplete the antibody protein. The main challenge of implementing the depletion strategy in MRM quantification was achieving good linearity and reproducibility. HCPs may co-precipitate with DS after reduction and alkylation, thus affecting the recovery and linearity. In the initial assessment, sensitivity of 0.8 ppm (LLOQ) and $R^2$ of above 0.99 were reached at five concentration levels ranging from 0.8 ppm to 500 ppm (results not shown). To further improve the sensitivity, the workflow was optimized through several experiments. The starting materials amount, injection amount and gradient were optimized.

Figure 5A:
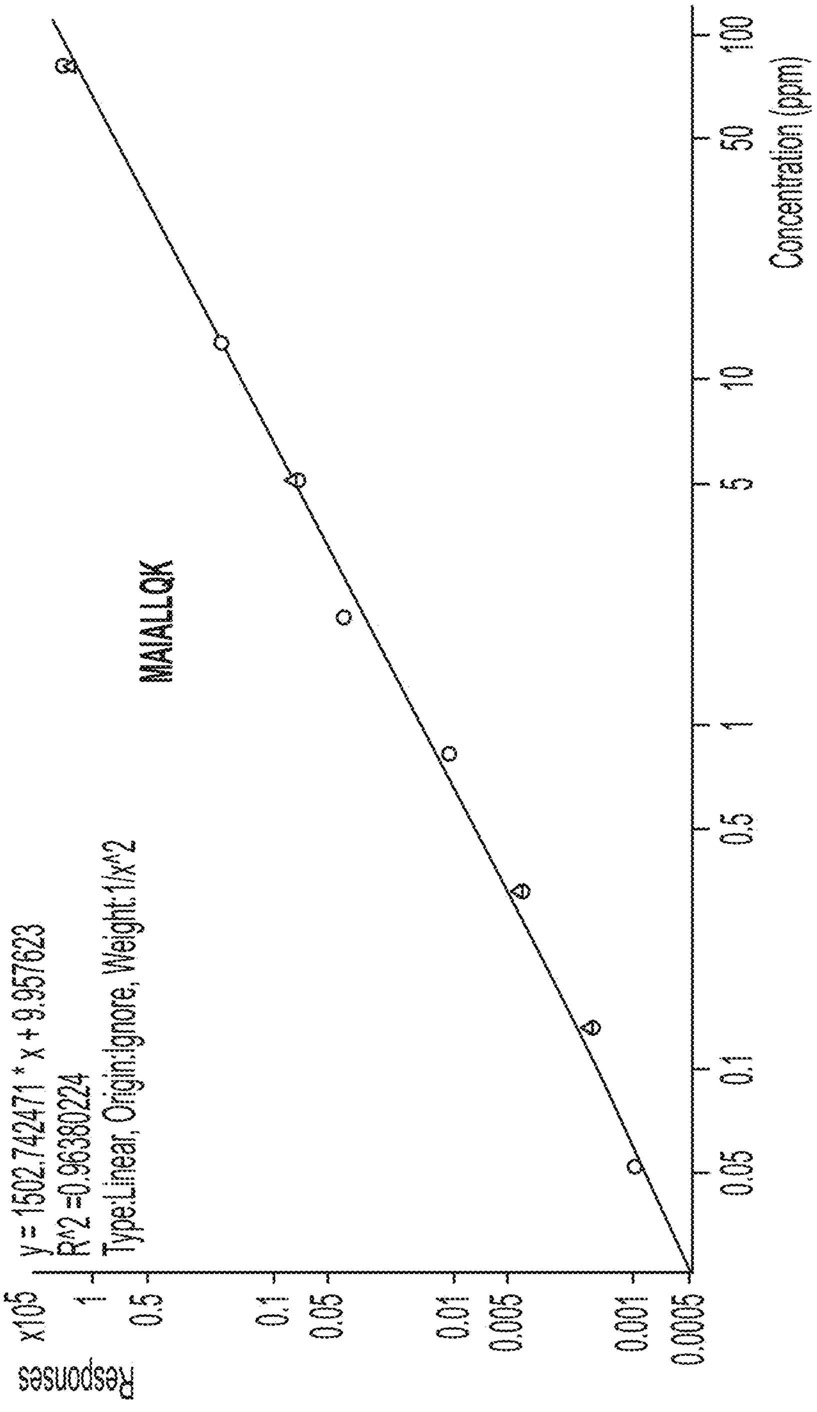
FIG. 5A shows a standard curve for MAIALLQK from native digestion, the linear regression and R square according to an exemplary embodiment.
Figure 5B:
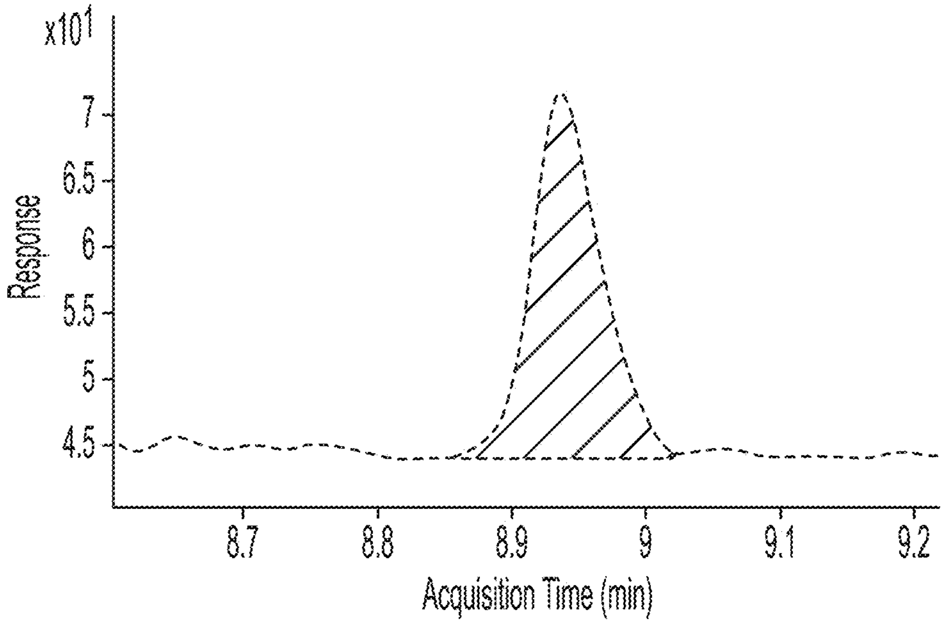
FIG. 5B shows an extracted in chromatograms (EIC) of MAIALLQK at 0.05 ppm.
Figure 5C:
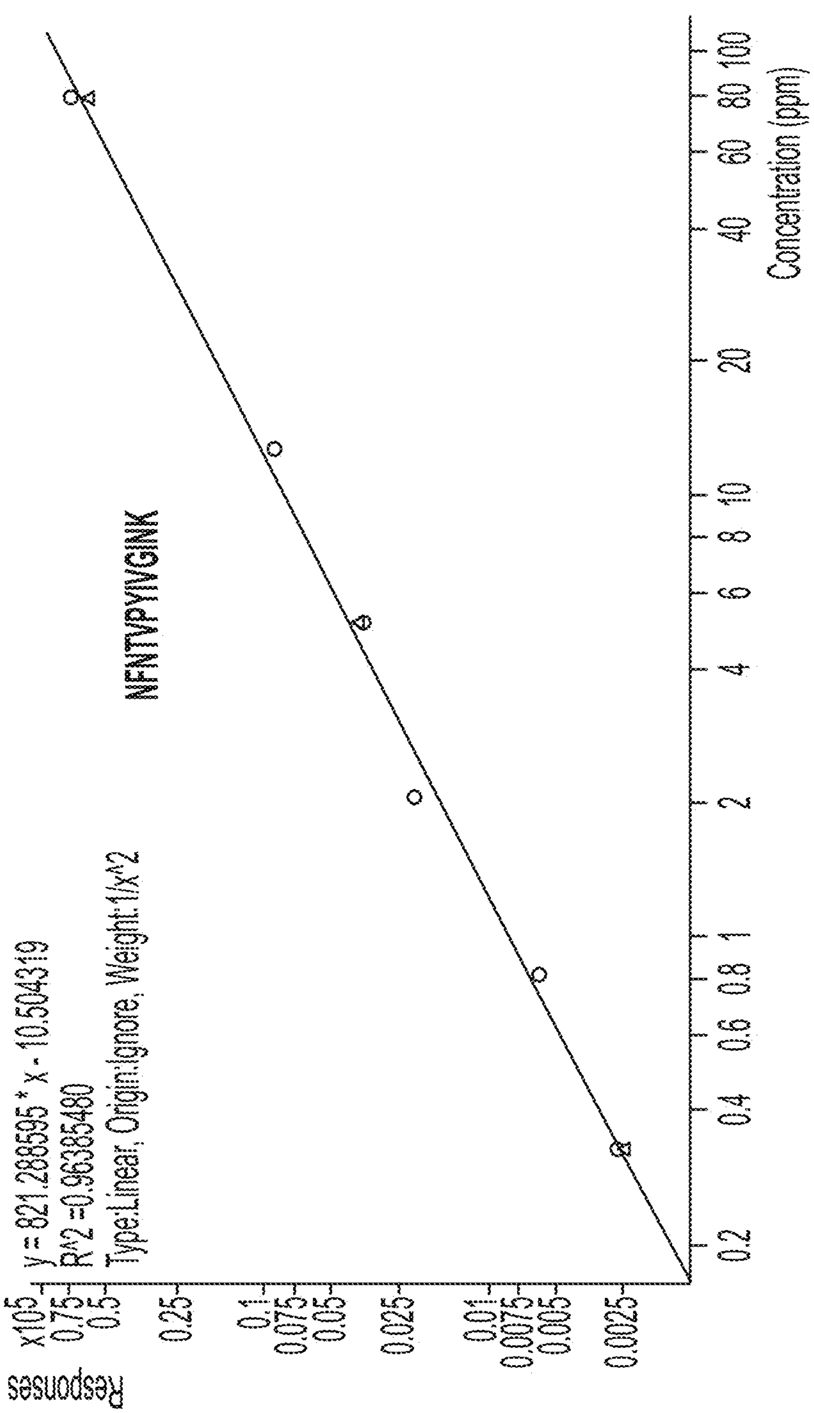
FIG. 5C shows a standard curve for NFNTVPYIVGINK from native digestion, the linear regression and R square according to an exemplary embodiment.
Figure 5D:
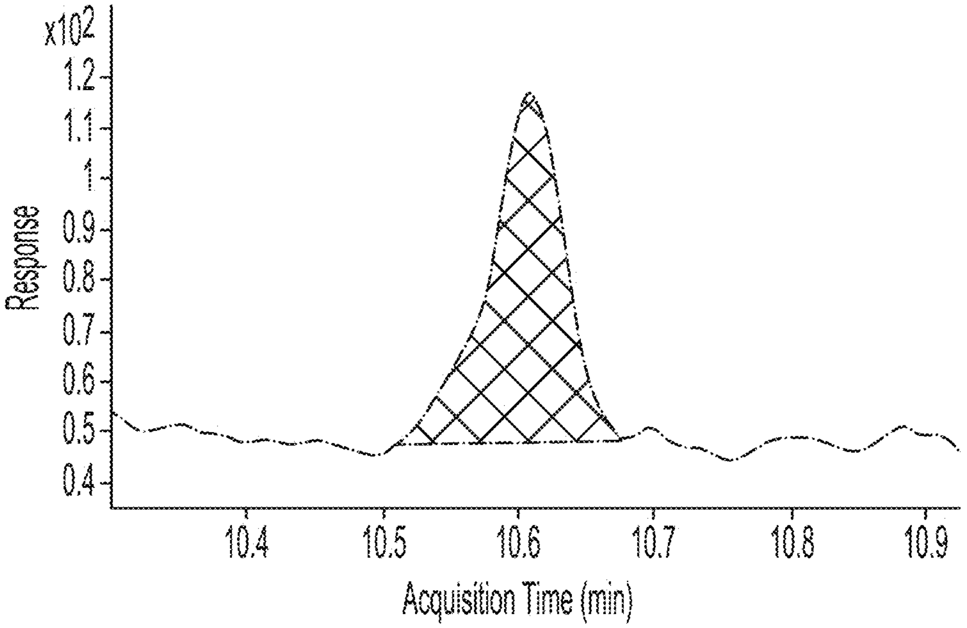
FIG. 5D shows an extracted in chromatograms (EIC) of NFNTVPYIVGINK at 0.3 ppm.

Under optimum condition, 0.05 ppm of LLOQ was achieved for CES'1-like' and 'B-1-like' isoforms (MAIALLQK). The dynamic range of curve was narrowed to 0.05-80 ppm and linearity with $R^2$ of 0.96 was obtained (FIG. 5*a*, Table 2). The combination isoforms (NFNTVPYIVGINK) included in the optimized MRM assay have slightly higher LLOQ (0.3 ppm) and calibration curve ranging from 0.3 to 80 ppm with $R^2$ of 0.96 (FIG. 5*c*, Table 2). The LLOQs of major isoforms ('1-like' and 'B-1-like') and combination isoforms were 0.05 ppm and 0.3 ppm, respectively (Table 2). By combining native digestion and MRM methods, the sensitivity of CES from the direct assay was improved from 2.0 ppm to 0.05 ppm. The LLOQ was two orders of magnitude lower than the conventional direct digestion-MRM method, and the sensitivity was sufficient to monitor the CES levels in mAb1 for supporting purification process development.

TABLE 2

Low limit of quantitation (LLOQ) and linear range of the CES HCP quantitation method

| Protein | Peptide | LLOQ (ppm) | Linear Range (ppm) |
|---|---|---|---|
| Liver carboxylesterase B-1-like, Liver carboxylesterase 1-like | MAIALLQK | 0.05 | 0.05-80 |
| Liver carboxylesterase B-1-like, Liver carboxylesterase 1-like, Liver carboxylesterase 1, Liver carboxylesterase 4, Carboxylic ester hydrolase | NFNTVPYIVGINK | 0.3 | 0.3-80 |

Example 7

Quantification of Liver Carboxylesterase in mAb1

The developed MRM method was utilized to monitor the CES levels in mAb1produced from the optimized purification process. Based on HCP profiling of mAb1, CES levels in the later process lots were less than 2 ppm (data not shown). However, the CES levels were estimated by comparing the HCP peptides to internal peptides, which underestimate ionization efficiency and digestion differences. To accurately measure CES present in the new process lots, the newly developed targeted native digestion-MRM assay was applied (Table 3). 2.3 ppm of liver carboxylesterase was quantified in 'Development-1' lot and comparable to HCP profiling results. In addition, minute levels of the HCP were also detected in 'Development-2' and 'Development-3' lots, but not detected by HCP profiling method. Although the levels were below LLOQ in 'Development-2/3', the % CV from the triplicate analysis was within 20%. Besides monitoring the abundance of CES, mAb1 FDS stability study was performed to evaluate PS80 degradation from selected mAb1 DS lots. Among the studied lots, 16% of PS80 degradation was observed in the FDS of 'Development-1', which contained 2.3 ppm of liver carboxylesterase. In the FDS of 'Development-2' and 'Development-4', no noteworthy levels of CES nor PS80 degradation was detected.

TABLE 3

| Concentration of CES in six mAb1 batches by MRM | | |
|---|---|---|
| mAb1 FCP/DS | ppm | CV (%) |
| Development-1 FCP | 2.3 | 2.3 |
| Development-2 FCP | 0.01* | 19 |
| Development-3 FCP | 0.03* | 11 |
| Development-4 FCP | ND | — |
| Development-5 DS | ND | — |
| Development-6 DS | ND | — |

There is an increasing need to develop sensitive, accurate and high-throughput analytical methods to monitor HCP clearance during therapeutic protein development. The present invention covers methods to identify and quantify a high-risk lipase HCP, CES, which is present at a low abundance level and is challenging to be quantified by routine LC-MS-based proteomics method. The workflow can be applied to investigate the root cause of PS80 degradation, facilitate downstream process development and effectiveness to remove high-risk HCP. This highly sensitive LC-MS/MS-MRM method that incorporates native digestion and DS depletion was developed to monitor the CES levels from several processes. While the direct digestion method coupled with MRM is not sufficient to monitor lipases at an active level, the newly developed native digestion-MRM method of the present invention has adequate sensitivity and is able to provide accurate quantitation. The HCP analysis strategy can be readily applied to monitor other high-risk HCPs with a sensitivity at sub-ppm or ppb levels.

What is claimed is:

1. A method for identifying at least one host-cell protein in a sample matrix including a protein of interest, comprising:

(a) adding a digestion agent under native conditions to obtain a native digested sample; and (b) analyzing the native digested sample using a triple quadrupole mass spectrometer to identify a peptide specific to said at least one host-cell protein, wherein said triple quadrupole mass spectrometer is run to obtain multiple reaction monitoring for at least one precursor-product ion for said peptide, wherein the lower limit of quantification of the method is less than about 1 ppm.

2. The method of claim 1, wherein said digestion agent is trypsin.

3. The method of claim 1, wherein said digestion agent is about 0.4 μg of trypsin.

4. The method of claim 1, wherein said native conditions include using said digestion agent such that said protein of interest is digested less than said host cell protein.

5. The method of claim 1, wherein said triple quadrupole mass spectrometer is coupled to liquid chromatography.

6. The method of claim 1, wherein said mass spectrometer is run in a positive mode.

7. The method of claim 1 further comprising performing enrichment of said at least one host cell protein.

8. The method of claim 1 further comprising performing depletion of said protein of interest.

9. The method of claim 1, wherein said host cell protein is liver carboxylesterase.

10. A method for quantifying at least one host-cell protein in a sample matrix including a protein of interest, comprising:

(a) adding a digestion agent under native conditions to obtain a native digested sample;

(b) analyzing the native digested sample using a triple quadrupole mass spectrometer to identify a peptide specific to said at least one host-cell protein, wherein said triple quadrupole mass spectrometer is run to obtain multiple reaction monitoring for at least one precursor-product ion for said peptide;

(c) quantifying an amount of said at least one host-cell protein by quantifying an amount of said peptide by utilizing an isotopically-enriched peptide having the same amino acid sequence as that of said peptide to calibrate the quantitation of said peptide, and utilizing a standard comprising a known concentration of peptide to calibrate the quantitation of said peptide.

11. The method of claim 1, wherein said host cell protein is liver carboxylesterase, and said protein of interest is an antibody.

12. The method of claim 11, wherein said digestion agent is trypsin.

13. The method of claim 11, wherein said native conditions include using said digestion agent such that said protein of interest is digested less than said host cell protein.

14. The method of claim 11, wherein said triple quadrupole mass spectrometer is coupled to liquid chromatography.

15. The method of claim 11, wherein said mass spectrometer is run in a positive mode.

16. The method of claim 11, further comprising performing enrichment of said at least one host cell protein.

17. The method of claim 11, further comprising performing depletion of said protein of interest.

18. The method of claim 12, wherein the trypsin is added to digest the sample matrix overnight at 37° C.

19. The method of claim 1, wherein said host cell protein is liver carboxylesterase, and said peptide is MAIALLQK or NENTVPYIVGINK.

20. The method of claim 1, wherein said protein of interest is an antibody, said host cell protein is liver carboxylesterase, and said peptide is MAIALLQK or NFNTVPYIVGINK, and wherein the method further comprising a step of depletion of the antibody after step (a).

* * * * *